United States Patent [19]
Voisin

[11] Patent Number: 5,019,109
[45] Date of Patent: May 28, 1991

[54] MULTI-AXIAL ROTATION SYSTEM FOR ARTIFICIAL ANKLE

[76] Inventor: Jerome P. Voisin, 143 "B" Isle of Cuba Road, Schriever, La. 70395

[21] Appl. No.: 492,885

[22] Filed: Mar. 9, 1990

[51] Int. Cl.$^5$ ............................. A61F 2/66; A61F 2/68
[52] U.S. Cl. ........................................ 623/49; 623/52; 623/55
[58] Field of Search ...................................... 623/47-55

[56] References Cited

U.S. PATENT DOCUMENTS

| | | | |
|---|---|---|---|
| 2,357,893 | 9/1944 | Harrington | 623/49 |
| 4,364,128 | 12/1982 | Mummert | 623/50 X |
| 4,605,417 | 8/1986 | Fleischauer | 623/49 |

*Primary Examiner*—Ronald Frinks
*Attorney, Agent, or Firm*—Pravel, Gambrell, Hewitt, Kimball & Krieger

[57] ABSTRACT

An artificial ankle system which is mounted within an artificial foot, such as a S.A.C.H. foot, with the ankle system comprising upper and lower plates, having a pair of spaced apart solid compressible members known as bonded rubber springs, which are attached to the upper and lower plates via gluing or the like, the rubber spring and plate system boltingly attached to the lower portion of the foot, and attached to a prosthesis to the upper prosthetic portion of the leg. This system further provides at least a posterior strap member secured around the upper and lower plate, the strap member serving as a means for compressing the posterior rubber spring to a certain degree, so that it is pre-compressed while being utilized in static or standing position, but allowing the rubber spring to also function in tension or elongation to a predetermined point. There may be further included an anterior strap, which likewise would compress the anterior spring as a strap that is fitted around the upper and lower plates. Those portions of the upper and lower plates resting above the anterior rubber spring.

15 Claims, 4 Drawing Sheets

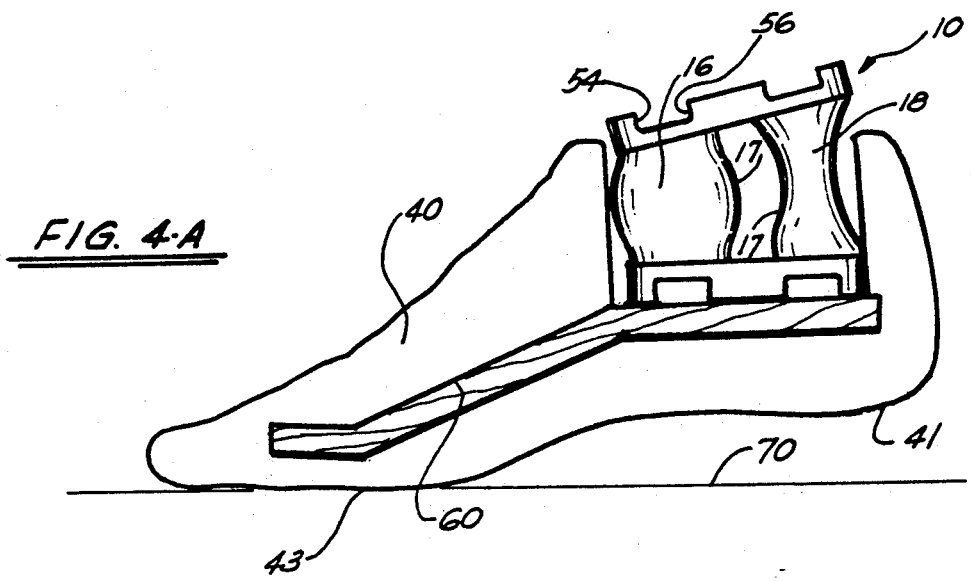
FIG. 4·A
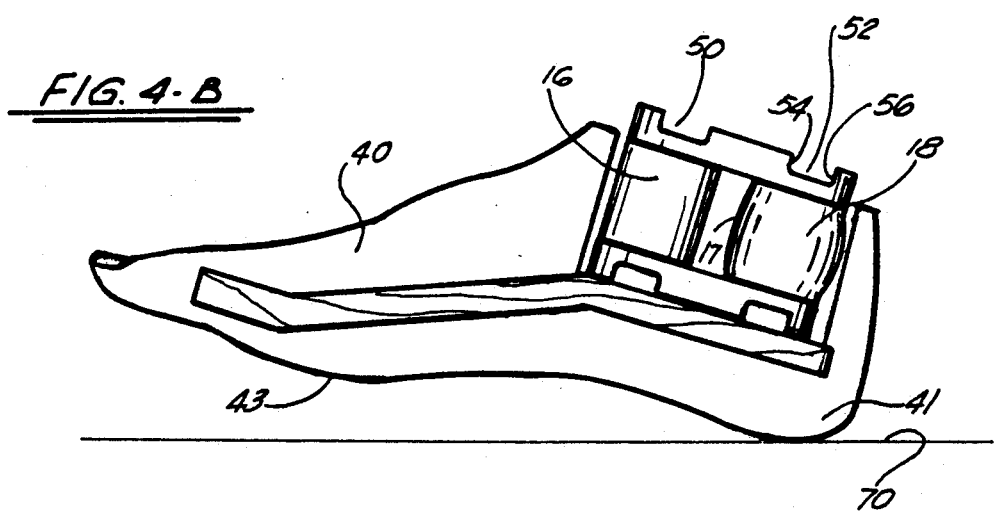
FIG. 4·B
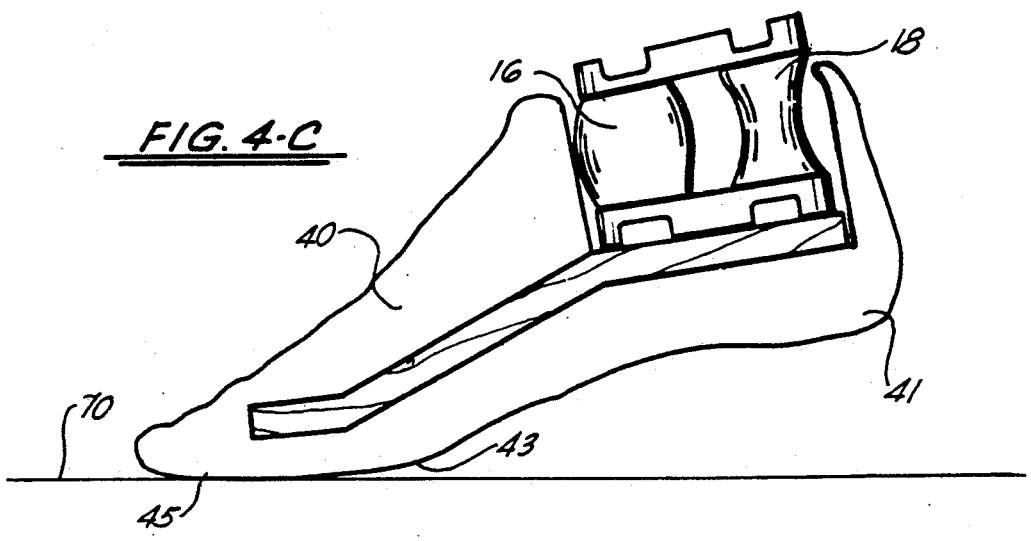
FIG. 4·C

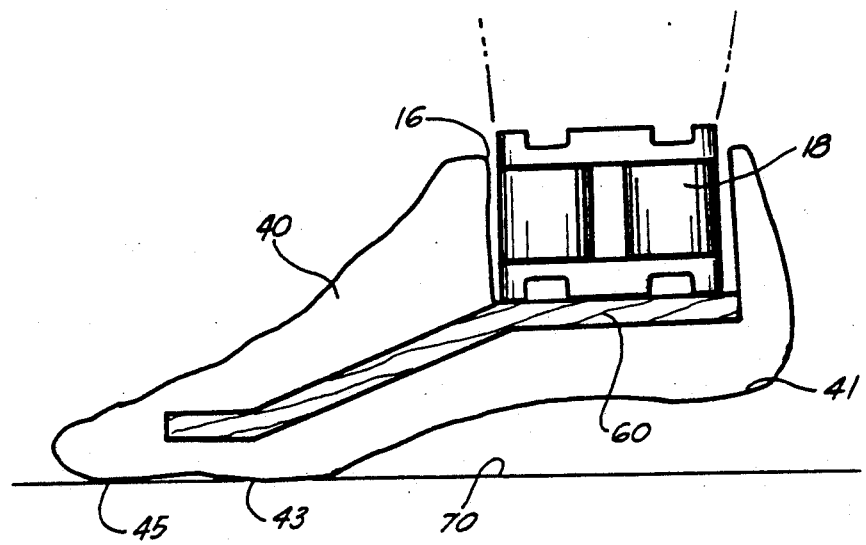
FIG. 4-D
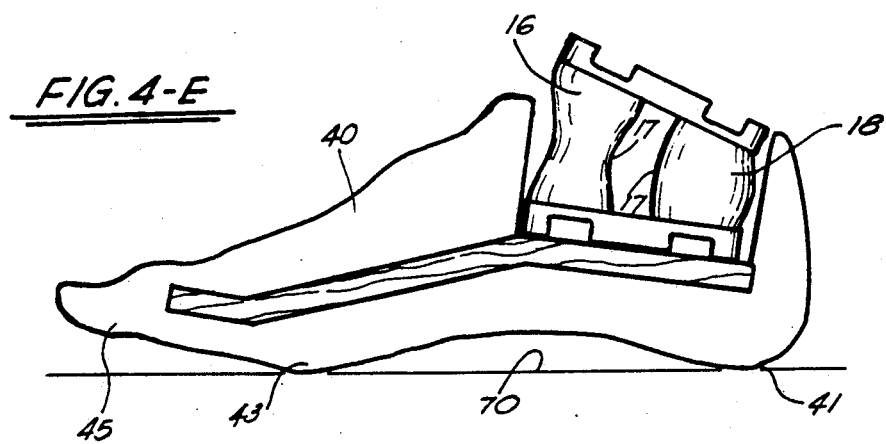
FIG. 4-E
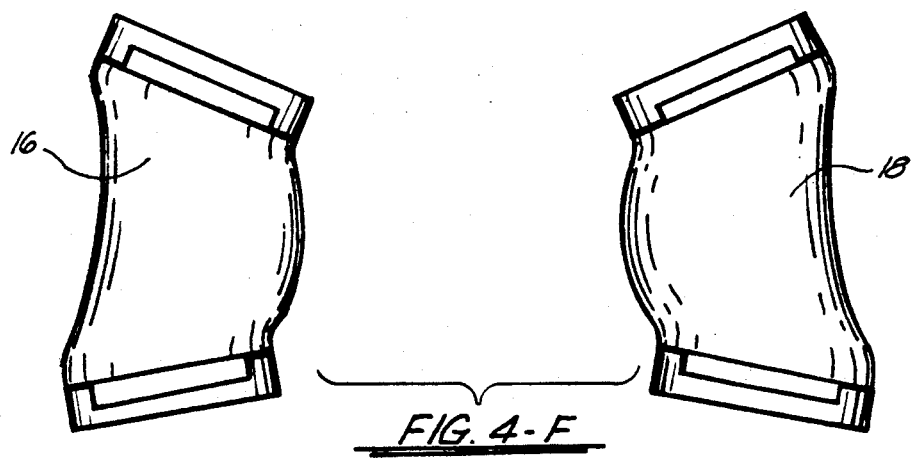
FIG. 4-F

MULTI-AXIAL ROTATION SYSTEM FOR ARTIFICIAL ANKLE

BACKGROUND OF THE INVENTION

1. Field of the Invention

The apparatus of the present invention relates to prosthetic feet and ankles. More particularly, the present invention relates to an artificial prosthetic device which provides multi-axial rotation for an artificial ankle mounted on an artificial foot.

2. General Background

In area of prosthetic limbs, artificial feet and ankles normally been constructed as a solid ankle cushion heel foot known as a S.A.C.H. foot attached or mounted to a limb along an approximate hinge axis taken through the ankle. It is critical that the foot and the ankle in artificial limbs operate as a single unit, in order to result in the proper bio-mechanics of the entire lower limb in assisting the wearer in walking and of the movement. The conventional S.A.C.H. foot has been the most widely prescribed artificial foot over the past thirty (30) years. The S.A.C.H. foot provides a stable base for a prosthesis, and addresses the concept of absorbing and storing energy as the heel of the foot strikes the surface and gradually releasing the energy through the remainder of the gate cycle. The newer S.A.C.H. foot has become known as a "energy storing foot". As new lightweight composite materials become available, energy storing feet become a practical alternative to the convention S.A.C.H. feet. Propulsion is provided by using a leaf spring mechanism inside a plastic shell of the artificial foot that stores and releases energy. This assists the amputee during the gait cycle by providing lift and thrust for the prosthesis.

Applicant has obtained U.S. Pat. No. 4,718,913 entitled "Dual, Ankle, Springs Prosthetic Foot and Ankle System", which provides a dual ankle spring foot/ankle system having a first and second helical springs attached to a top ankle plate and distally to a plantar base plate. The anterior and posterior springs are attachably engaged to the plates through a helical nut for helically engaging the spring around its body portion and attaching the spring to the plates themselves. The helical attachment loses no flexion as would occur with welding or the like. Further it provides the necessary propulsion and movement of the ankle in combination with artificial feet, such as the S.A.C.H. foot.

SUMMARY OF THE PRESENT INVENTION

The prosthetic ankle/foot combination of the present invention relates to an improvement in the patented system in the U.S. Pat. No. 4,718,913, in that it provides an artificial ankle system which is mounted within an artificial foot, such as a S.A.C.H. foot, with the ankle system comprising upper and lower base plates, having a pair of spaced apart solid compressible members known as bonded rubber springs, which are attached to the upper and lower plates via gluing (adhering) or the like, the rubber spring and plate system boltingly attached to the lower portion of the foot, and attached to a prosthesis to the upper prosthetic portion of the leg. This system further provides at least a posterior strap member secured around the upper and lower plate, the strap member serving as a means for compressing the posterior rubber spring to a certain degree but also allows the rubber springs to act in tension or elongation to a predetermined point. There may be further included an anterior strap, which likewise would compress the anterior spring as a strap that is fitted around those portions of the upper and lower plates resting above the anterior rubber spring.

Therefore, it is the principal object of the present invention to provide an artificial ankle system having anterior and posterior rubber compression springs attached to upper and lower plates secured within an artificial foot;

It is still a further object of the present invention to provide a multi-axial rotation system for an artificial ankle which may attach to the foot via an allen bolt or a threaded bolt depending on whether the upper or lower plate is mounted to the lower portion of the foot;

It is still a further object of the present invention to provide an artificial ankle prosthesis which may be used within a Symes-type prosthetic foot;

It is still a further object of the present invention to provide a prosthetic ankle system which incorporates a dynamic elastic response in all planes of motion including rotation or shear;

It is still a further object of the present invention to provide a prosthetic ankle system which may have different strength in the rubber compression springs in the system depending on the weight and the activity levels of the amputee;

It is still a further object of the present invention to provide a multi-axial system for artificial ankles which incorporate rubber compression springs bonded to reversible adapters which allows the adaptors to be bolted to the ankle plate and therefore function with the maximum efficiency in all planes of motion i.e., compression, tension and shear; and It is still a further object of the present invention to provide a artificial ankle system which may incorporate posterior and anterior compression bands for pre-compressing the rubber compression springs during use of the system in a static (standing) position.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIGS. 4A-4F represent plan elevational views of the apparatus of the present invention mounted in an artificial foot as the foot is undergoing various movements during the walking motion.

DETAILED DESCRIPTION OF THE PREFERRED EMBODIMENT

Figure 1:
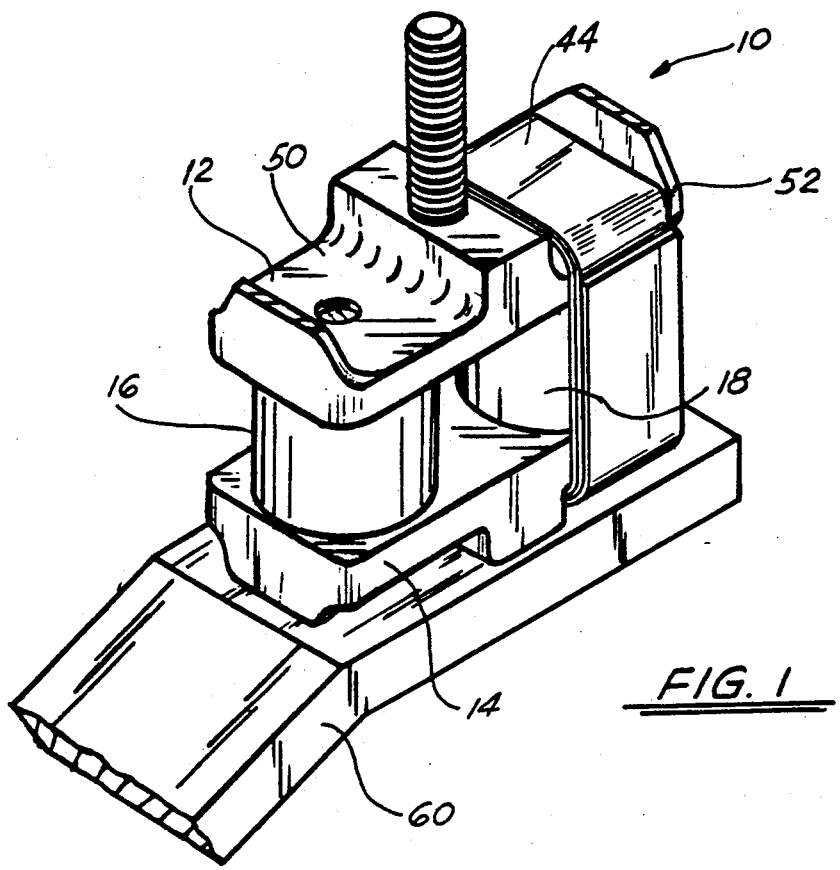
FIG. 1 illustrates the preferred embodiment of the apparatus of the present invention.

The preferred embodiment of the apparatus of the present invention is illustrated in FIG. 1 by the numeral 10. Apparatus 10, for purposes identification is identified as a multi-axial rotation system for artificial feet or in shorthand a "M.A.R.S." unit. M.A.R.S. unit 10, as illustrated, comprises a first upper plate 12, a second lower plate 14, and a first anterior rubber compression spring 16 and a second posterior rubber compression member 18; members 16, 18 positioned intermediate plate or platform members 12 and 14, to form the principal components of the composite ankle system 10 as illustrated. For purposes of construction, upper and lower plate or platform members 12 and 14 are reversible in their use.

Figure 3:
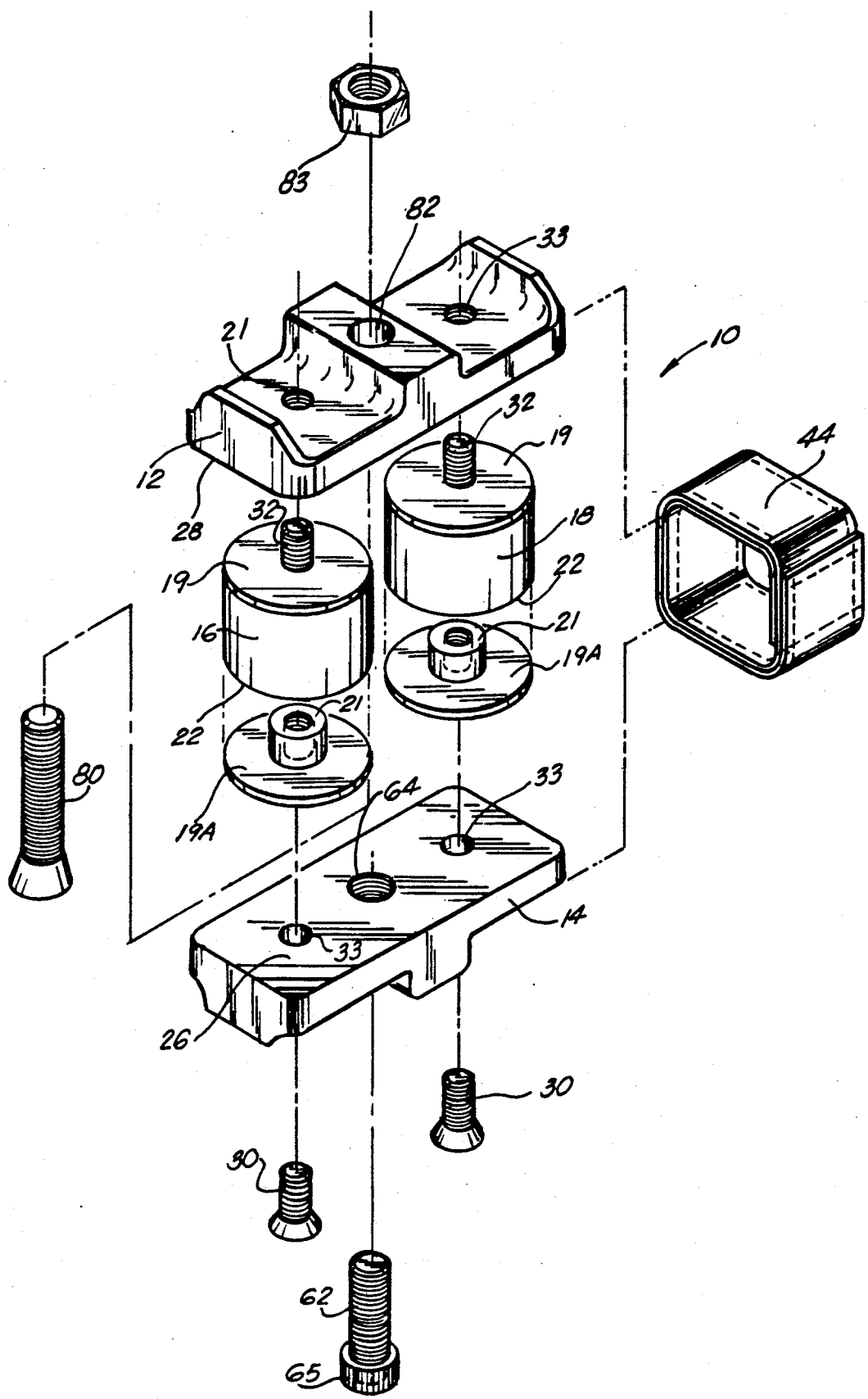
FIG. 3 illustrates an exploded view of the preferred embodiment of the apparatus of the present invention.

As further illustrated in FIG. 3, anterior compression member 16 and posterior member 18 are substantially circular in cross-section, having an upper male threaded screw 32 bonded to compression members 16, 18 and having lower female threaded indented area, on each of the compression members 16, 18. It should be noted, the upper and lower of faces 19, 22 of members 16, 18 are positioned against the lower surface 26 of lower plate member 14 and the lower surface 28 of upper plate 12 as illustrated in FIG. 1. For purposes of attachment, rubber compression members 16, 18 are fixedly engaged to the surfaces 26, 28 of plate members 12, 14 via upper bolt 32 onto threaded ports 21 of plate 12, or adhesive bonding, an adhesive bonding material connect the attachment plates 12, 14 to these rubber members 16, 18 to allow lateral flexing of members 16, 18 or via bolting and posterior adhesive bonding only. It is this fixation to top and bottom plates 12, 14 that is a principal difference between all previously used memory block type ankle units. There is further included means positioned on the upper platform member for securing the apparatus to the ankle, shank, or lower end of the prosthetic device portion of the wearer of the apparatus.

The rubberized compression spring members 16, 18 are of the type manufactured by Lord Industrial Products and are bonded rubber springs constructed of bonded natural rubber compounds which may be natural rubber or a synthetic rubber which are able to transmit a dynamic load, absorb energy, or dissipate energy as the case may be and return these energies.

Since there are no rigid posts or bolts through members 16, 18, the bonded rubber springs permit motion between supporting and supported members in all planes of motions. The springs provide flexibility designed to allow motion without overstressing the components in which the springs are utilized. They also eliminate the need for lubrication by acting as joints or connections to accommodate functional oscillations or deflexions. The preferable type of spring mounts utilized would be the sandwitch type mount which isolate vibration, absorb shock and atenuating noise due to structure borne vibrations. This construction would assure the proper installation of the mount and improve fatigue life over unbonded designs. Pre-compression of the flexing element (as will discussed further) takes place when the anterior of posterior compression bands are applied over plates 12 and 14, or as with the present invention through the use of anterior or posterior compression bands as will be discussed further.

Figure 2:
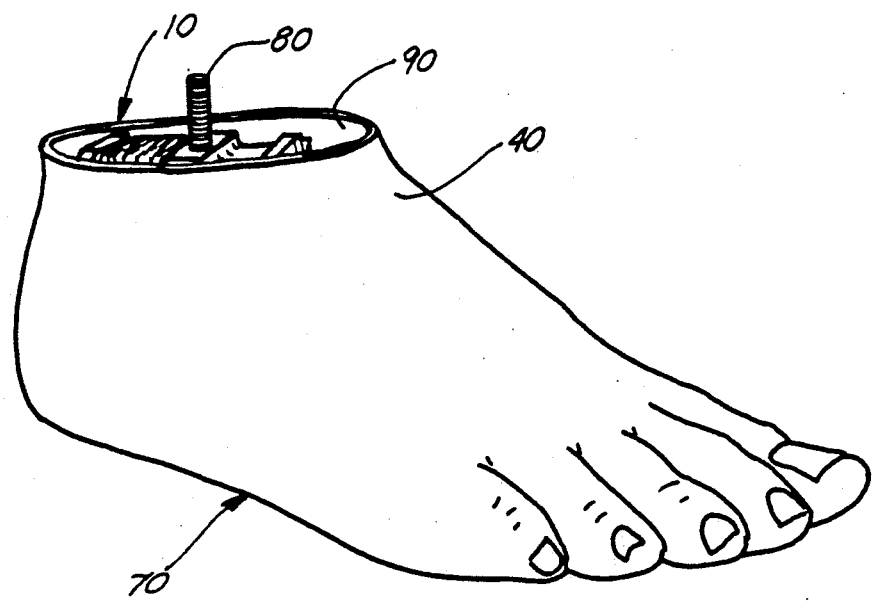
FIG. 2 illustrates the preferred embodiment of the apparatus of the present invention as mounted in a typical artificial foot such as a Symes foot.

As further illustrated in FIG. 1, once bonded into position upon intermediate plate members 12, 14, as illustrated, the anterior member 16, or posterior member 18, may be pre-compressed prior to being installed into an artificial foot 40 as illustrated in FIG. 2. This pre-compression is provided by a means which s defined as a compression band 44, as illustrated in FIGS. 1 and 3. Band 44 is constructed of a flat fabric which is sold under the trademark CORDURA nylon owned by Dupont, and is a flexible fabric. The compression member as illustrated in FIG. 3, would be wrapped around as a continuous wrap between the upper plate member 12 and the lower plate member 14, so that band 44 is maintained in position, each of the plate members 12, 14 include an anterior milled or slotted area 50 and posterior recess area 52 spanninq the width of the plates 12 and 14 as illustrated. The recessed areas 50, 52 are substantially the width of the compression member 44, so that with each of the recess areas have upper extending end walls 54, 56 so that when the compression member 44 is wrapped around the heel component 10, as illustrated in FIG. 1, compression member 44 is held in position within recess area for example 52 as seen in FIG. 1, and a slippage of a member can be avoided.

The component 10, as seen in FIG. 1 fully assembled, is mounted onto deflection plate 60, which is positioned within foot 40 or is already a fixed part of foot 40, along the length of foot 40 (as illustrated in phantom view in FIG. 2), so as to serve as a long flexible lever arm that may provide appropriate leaf spring for a fluid transition through the gait cycle.

As seen in FIG. 3, the mounting of apparatus 10 onto plate 60 is provided by several methods. The first method is the use of allen or hex headed bolt nut 62 threaded into a centrally located port 64 in the base of lower plate 14, with the lower end 65 of bolt 62 extending flush or countersunk into the bottom 70 of foot 40, which would secure apparatus 10 in place as seen in FIG. 1. Due to the shortened length of bolt 62, bolt 62 would only extend up to a point substantially flush with the upper surface 26 of plate 14 when in place. Likewise, the upper plate 12 would be attached via a second bolt 80 secured into plate 12, and attached to the upper leg portion of the artificial limb, using nut 83, or the existing threaded section in the prosthesis. In addition, nut 83 may be used to attach an artificial foot when the MARS unit is used in the upsidedown configuration. Thus, the upper plate 12 and lower plate 14 would be secured onto both the foot and the upper leg portion respectfully.

Turning now to the construction of the apparatus 10, there is first provided the pair of compression members 16 and 18, secured intermediate the lower surface 28 of upper plate 12, and the upper surface 26 of lower plate 14. This means of attachment would include on the upper side of compression members 16 and 18, a disc member 19 bonded to the rubber compression members 16, 18, via glue or the like, each of the disc 19 having a bolt portion 32 extending upward therefrom, through ports 33 in upper plate 12, and threadably engaged into ports 33. Likewise, there would be further included a pair of lower disc 19A secured to the lower surface of each of the compression members 16, 18, with each of the disc 19A having an upper depending threaded mounts 21, each of which are insertable into a lower port (not illustrated) in each compression member 16, 18, so that the lower surface 22 of each of the compression members may bondingly adhere to the plates 19A via glue or the like, yet serve as a means for accommodating a pair of bolts 30 through ports 33 in lower plate 14, and to threadably engage within portions 21. Therefore, in full configuration, as illustrated in FIG. 1, the compression members 16, 18, while yet secured to upper plate 12 and lower plate 14, have no rigid bolt or the like through their body portions, and therefore are able to move in the manner as illustrated in FIGS. 4A through 4F, as will be illustrated. As was further discussed, when the component has been bolted together member 44 may be secured through the upper and lower plates, as was discussed more fully in FIG. 1.

Therefore, as illustrated in FIG. 2, in that particular embodiment, it would appear that the apparatus 10 has been positioned within a hollow 90 in the upper portion of a Symes foot 40 when the lower bolt or allen bolt threadably engaged into the lower portion of the Symes foot 40 for mounting thereinto. After the upper bolt 80 would be threadably engaged into the upper leg portion of the prosthetic combination of the amputee, it would be properly mounted onto the base plate 60 located in foot 40.

FIGS. 4A-4F represent the various dynamic movements of the apparatus during the gait movement of a foot during walking. As illustrated in FIG. 4A, there is illustrated foot member 40 having apparatus 10 mounted onto base plate 60. In this particular embodiment, the apparatus is seen without the use of the anterior or posterior compression bands 44, so that a clear view of the movement of compression springs 16 and 18 may be viewed in full view. However, for purposes of the actual combination, in all likelihood there would either be a posterior compression band 44 MARS unit may function with anterior band missing but it cannot function with just an anterior band, for safety it is best to have both bands, or both in combination with the apparatus.

As illustrated in FIG. 4A, in this particular illustration, the foot is positioned in the heel off position i.e., with the heel 41 of foot 40, moved off of a surface 70 and the ball 43 of the foot 40, striking the surface 70. In this illustration it should be noted that due to the shifting of the weight of the amputee when the foot is placed in this position, the anterior compression member has been compressed with the sidewall 17 bulging outward under the force of the compression, yet at the same time the posterior compression member 18 has be stretched so that the sidewall 17 forms a concave shape as the compression member 16 is being expanded through the movement of the ankle.

FIG. 4B would illustrate the heel 41 striking the surface 70, with the ball 43 of the foot 40 raised off of the surface. In this particular movement of the gait, the posterior compression spring 18 is being compressed with the sidewall 17 expanding outward, and the anterior compression member 16 is non-compressed, and in the normal unstressed position.

In FIG. 4C the foot is in the position where the toe 45 is striking the surface 70, with the ball 43 and heel 41 of foot 40 moved off of the surface. In this position, again the posterior compression member 18 is stretched inwardly, with the anterior member 16 compressed but not as severely as seen in FIG. 4A when the ball of the foot is striking, because energy is being returned propulsion.

In 4D, the foot 40 has moved to mid-stance, so that the ball 43 and toe 45 are lying flat on surface 70, with heel 41 raised off of surface 70 for normal shoe heel height. In this position the weight of the wearer of the prosthesis is directly on both of the compression members and therefore each of the compression members 16, 18 are non-stressed, and are in the normal non-stressed position as seen in FIG. 4D.

In FIG. 4E, the foot is in the "flat foot" position with the heel 41 and ball 43 of foot 40 striking the floor, with the toe 45 raised off of the surface 70. In this position, which is the opposite of the stressing as undertaken in 4A, the anterior member 16 is stretched inwardly so that wall 17 forms a concave central portion with the posterior member 18 compressed so that the wall 17 is bulging outwardly as indicated.

For purposes of further illustration, 4F illustrates the anterior member 16 and posterior member 18 as each is undergoing inversion and eversion respectively during the wearing of the apparatus. This particular view of the springs indicates the movement of the compression members 16, 18 while this stress is being placed there upon.

Again to reiterate, the components of the D.A.S. M.A.R.S. unit, as illustrated in FIGS. 4A-4E do not illustrate the use of the anterior or posterior compression bands 44. With the use of compression bands 44 in place, as seen in FIG. 1, the stretching of the anterior or posterior member 16, 18 is restricted, in that each of the members are pre-compressed when the band is in place, and therefore undergo minimum stretching as the case may be. This is done so that the wearer is given predetermined amount of movement of the compression members while going through the walking gait when being worn.

In addition, the top and bottom plates, with anterior and posterior members 16 and 18 mounted therebetween, may undergo a shear movement, in that the end of the plates are twisted yet due to the resilent factor of members 16, 18 allows the shear movement to return to its original alignment.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A multi-axial rotation apparatus for an ankle prosthesis positionable in an artificial foot, the system comprising:
   a) a first platform member secured to the artificial foot;
   b) a second platform member spaced apart from the first platform member and positioned in a common plane therewith;
   c) a first anterior solid compressible member bonded between and positioned intermediate first lower platform and upper platform members;
   d) a second posterior solid compression member likewise bonded between and positioned intermediate the upper and lower platform members;
   e) means interconnecting the first and second platform members and pre-compressing at least the posterior solid compression member; and
   f) means for attaching the prosthesis to an upper leg portion of a wearer of the apparatus.

2. The apparatus in claim 1, wherein the apparatus is boltingly attached to the floor portion of the artificial foot member.

3. The apparatus in claim 1, wherein the upper and lower platform members further provide recessed anterior and posterior recessed portions for accommodating a fabric compression band secured between the upper and lower platform members within the recessed portions.

4. The apparatus in claim 1, wherein the anterior and posterior solid compression members are formed of compressible rubber material.

5. The apparatus in claim 1, wherein the anterior and posterior compression members act both in tension and in compression during walking with the apparatus.

6. The apparatus in claim 1, wherein the solid anterior and posterior solid compression members provide means for extending or compressing the platform members during the walking gait.

7. The apparatus in claim 1, wherein the means for securing the apparatus to the leg portion of the wearer comprises a bolt member extending upwardly from the upper platform member.

8. The apparatus in claim 1, wherein the upper and lower platform members are reversible.

9. An ankle prosthetic apparatus, positionable in a hollow of an artificial foot, the apparatus comprising:
   a) a lower platform member secured to the artificial foot via bolting or the like;
   b) an upper platform member spaced apart from the lower platform member, and positioned parallel to the lower platform member;
   c) a first anterior solid rubber compression member positioned intermediate and bonded or bolted to the upper and lower platform members;
   d) a second posterior solid rubber compression member likewise positioned intermediate and bonded or bolted to the upper and lower platform members;
   e) a compression band positioned around and interconnecting the posterior portions of the upper and lower platform members, the band pre-compressing at least the posterior solid rubber compression member;
   f) means positioned on the upper platform member for securing the apparatus to the ankle, shank, lower end of prosthesis device portion of the wearer of the apparatus.

10. The apparatus of claim 9, wherein there is further included a second compression band secured to and interconnecting the anterior portions of the upper and lower platform members to likewise pre-compress the anterior solid rubber compression member.

11. A multi-axial rotation system postionable in a hollow of an artificial foot or on top of the artificial foot, the system comprising:
   a) upper and lower spaced platform members;
   b) a first anterior solid compression member bonded or bolted to and positioned between the upper and lower platform members;
   c) a second posterior solid compression member positioned between and bonded or bolted to the upper and lower platform members;
   d) means for attaching the lower platform member to the artificial foot, so that during the walking gait, the compression members serve as a multi-axial rotation system; and
   e) means for precompressing at least one of the compression members.

12. The apparatus in claim 11 wherein during the mid-stance position of the foot, the anterior and posterior compression members are equally compressed, defining the normal stance.

13. The apparatus in claim 11, wherein in the foot flat portion of a walking gait, the anterior compression member is stretched beyond the normal stance, and the posterior compression member is compressed beyond the normal stance.

14. The apparatus in claim 11, wherein in the heel strike portion of a walking gait, the anterior compression member is in the normal stance, and the posterior compression member is compressed greater than the normal stance.

15. The apparatus in claim 11, wherein in the heel off position of a walking gait, the anterior compression member is compressed greater than the normal stance, and the posterior compression member is stretched greater than the normal stance.

* * * * *